(12) United States Patent
Rhodes et al.

(10) Patent No.: US 10,670,763 B2
(45) Date of Patent: Jun. 2, 2020

(54) SENSOR FOR DETERMINING SOIL MOISTURE

(71) Applicant: Deere & Company, Moline, IL (US)

(72) Inventors: Michael Rhodes, Richfield, MN (US); Kartheek Karna, Fargo, ND (US); Nikolai Tevs, Daytona Beach Shores, FL (US); Jeffrey S. Puhalla, Hawley, MN (US); Elijah B. Garner, Bettendorf, IA (US)

(73) Assignee: DEERE & COMPANY, Moline, IL (US)

( * ) Notice: Subject to any disclaimer, the term of this patent is extended or adjusted under 35 U.S.C. 154(b) by 0 days.

(21) Appl. No.: 15/435,791

(22) Filed: Feb. 17, 2017

(65) Prior Publication Data
US 2018/0239044 A1      Aug. 23, 2018

(51) Int. Cl.
*G01V 3/08* (2006.01)
*G01N 27/04* (2006.01)
(Continued)

(52) U.S. Cl.
CPC ........... *G01V 3/088* (2013.01); *A01G 25/167* (2013.01); *G01N 27/043* (2013.01);
(Continued)

(58) Field of Classification Search
CPC ...... G01V 3/088; G01N 27/048; G01N 33/24; G01N 33/245; G01N 33/246; G01N 27/043; G01N 27/223; G01N 27/041; G01N 27/121; G01N 19/10; G01N 1/08; G01N 1/28; G01N 2001/021; G01N 2021/1738; G01N 21/55; G01N 2203/0019;
(Continued)

(56) References Cited

U.S. PATENT DOCUMENTS 3,882,383 A    5/1975 Matlin
4,929,885 A    5/1990 Dishman
(Continued)

FOREIGN PATENT DOCUMENTS

EP    1174715 A2    1/2002
JP    2011013025 A  1/2011

OTHER PUBLICATIONS

Adamchuck, V.I. et al. "On-the-go soil sensors for precision agriculture". Jun. 12, 2014, 22 pages, University of Nebraska, Lincoln, Nebraska, USA.
(Continued)

*Primary Examiner* — Lee D Rodak

(57) ABSTRACT

A sensor for determining soil properties is disclosed herein. The sensor includes a ground engaging structure adapted for coupling to an agricultural implement and to penetrate soil at a predetermined depth. An electrode assembly is disposed on a sensing surface of the ground engaging structure that includes a plurality of electrode sensing units. The plurality of electrode sensing units are configured to selectively generate a series of electric fields that project outwardly into the surrounding soil in response to receipt of an excitation signal and sense changes in the electric field corresponding to a change in a measured electrical output signal that is used to determine one or more soil properties during movement of the agricultural implement in a field.

19 Claims, 6 Drawing Sheets

(51) Int. Cl.
*G01N 27/22* (2006.01)
*G01N 33/24* (2006.01)
*A01G 25/16* (2006.01)

(52) U.S. Cl.
CPC ......... *G01N 27/048* (2013.01); *G01N 27/223* (2013.01); *G01N 33/246* (2013.01); *G01N 2033/245* (2013.01)

(58) Field of Classification Search
CPC ........ G01N 3/48; A01B 79/005; A01B 79/02; A01B 76/00; A01B 49/06; A01B 49/04; A01B 69/007; A01B 69/002; A01B 35/02; A01B 63/008; A01B 63/1115; A01B 63/114; A01B 63/145; A01C 7/203; A01C 7/007; A01C 23/007; A01C 23/02; A01C 5/064; A01C 5/06; A01C 5/062; A01C 5/066; A01C 21/00; A01C 21/005; A01C 7/10; A01C 7/102; A01C 7/105; A01C 7/06; A01C 7/08; A01C 7/12; A01C 7/20; A01C 7/201; A01C 7/206; A01C 11/02; A01C 14/00; A01C 19/00; Y10S 111/903; A01M 7/0089; A01G 25/16
See application file for complete search history.

(56) References Cited

U.S. PATENT DOCUMENTS

| | | | | |
|---|---|---|---|---|
| 5,524,560 A | * | 6/1996 | Carter | ................. A01B 63/114 111/200 |
| 6,138,590 A | * | 10/2000 | Colburn, Jr. | ......... A01B 79/005 111/118 |
| 7,183,779 B2 | * | 2/2007 | Hughes | ................ G01N 33/246 324/664 |
| 9,585,301 B1 | * | 3/2017 | Lund | ........................ A01C 5/06 |
| 2002/0060576 A1 | * | 5/2002 | Tominaga | ........... G01N 27/048 324/715 |
| 2002/0165700 A1 | * | 11/2002 | Zur | ....................... A01G 25/165 702/188 |
| 2003/0009286 A1 | * | 1/2003 | Shibusawa | ........... A01B 79/005 702/2 |
| 2003/0016029 A1 | * | 1/2003 | Schuler | .................. A01B 35/32 324/643 |
| 2008/0202777 A1 | * | 8/2008 | Corcoran | ................ E02D 1/027 172/1 |
| 2014/0358381 A1 | * | 12/2014 | Holland | ................. G01N 21/55 701/50 |
| 2017/0094889 A1 | * | 4/2017 | Garner | ................... A01B 76/00 |

OTHER PUBLICATIONS

Thomas, A.M., "In situ measurement of moisture in soil similar substances by 'fringe' capacitance" J. Sci. Instrum., 1996, vol. 43, 8 pages. Retrieved on Jul. 20, 2016. Retrieved online <URL http://www.iopscience.iop.org>.

European Search Report issued in counterpart application No. 18152159.2, dated Mar. 23, 2018 (14 pages).

Office Action issued in counterpart application No. EP18152159.2, dated Jun. 11, 2019 (8 pages).

* cited by examiner

SENSOR FOR DETERMINING SOIL MOISTURE

TECHNICAL FIELD

The present disclosure generally relates to a sensor for determining soil properties as a function of depth.

BACKGROUND

In the farming industry, ensuring adequate soil conditions are maintained during the planting process is significantly important for maximizing crop yields. For example, improper temperature conditions or insufficient water and/or oxygen supply could lead to seed germination failure, thereby resulting in decreased crop yields. As such, if soil properties at various depths are known, proper soil conditions can be maintained. Also, in the case of seeding or planting seeds, seeds can be placed at optimal germination and emergence depths.

To address such concerns, some conventional approaches includes the use of portable sensing devices which are manually inserted into the ground to measure soil properties at fixed locations. Drawbacks to such designs include poor sensor resolution, limited sensing capabilities, as well as inadequate downforces, which leads to insufficient seed-to-soil contact. To overcome limitations associated with portable sensing devices, other conventional approaches include the use of sensing devices that are capable of measuring the soil moisture at various soil locations. Particularly, the sensor measures the moisture content of the soil at its surface. Drawbacks to such approaches, however, include increased costs, as well poor sensor resolution. Therefore, there is a need in the art for a low cost and high resolution sensing device that overcomes the drawbacks of the above conventional systems.

SUMMARY

In accordance with one embodiment, a sensor for determining soil properties that includes a ground engaging structure and electrode assembly disposed on a sensing surface of the ground engaging structure is provided. The ground engaging structure being adapted for coupling to an agricultural implement and to penetrate soil at a predetermined depth. The electrode assembly having a plurality of electrode sensing units that are adjacently arranged and spaced apart from one another in a generally parallel arrangement, wherein in response to receipt of an excitation signal the plurality of electrode sensing units are configured to induce generation of an fringing electric field across an output of each of the electrode sensing units to detect changes in the electric field corresponding to a change in a measured electrical output signal that is used to determine one or more soil properties during movement of the agricultural implement in a field.

BRIEF DESCRIPTION OF THE DRAWINGS

Like reference numerals are used to indicate like elements throughout the several figures.

DETAILED DESCRIPTION

Figure 1:
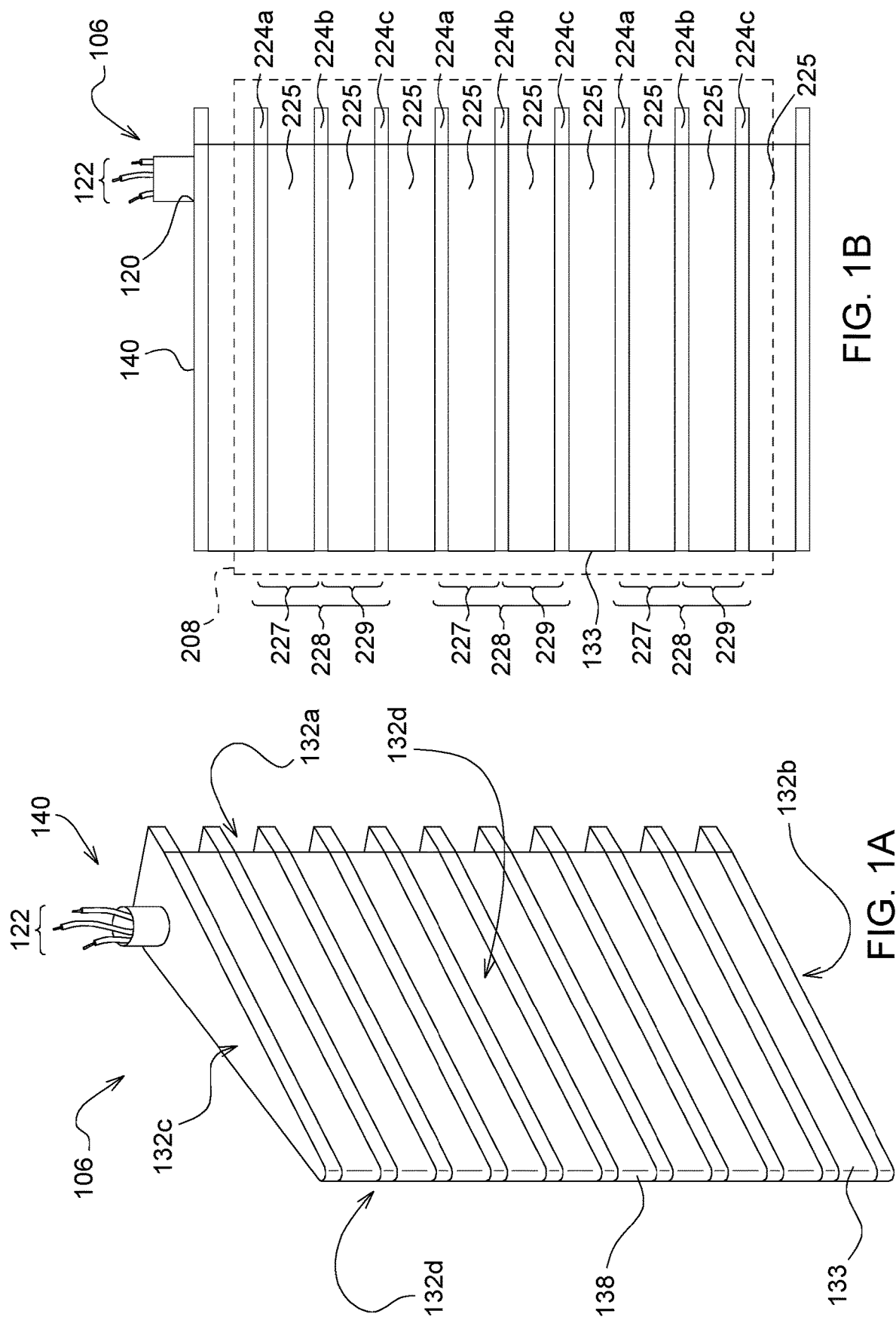
FIG. 1A is a perspective view of a sensor according to an embodiment.
FIG. 1B is a side view of a sensor according to an embodiment.

Referring to FIGS. 1A-1B, a sensor 106 for determining soil properties is shown according to an embodiment. In embodiments, the sensor 106 can comprise an electrode assembly 208 having a plurality of electrode sensing units 228 arranged in generally parallel relation to one another within a ground engaging structure 140. The ground engaging structure 140 may comprise a first and a second ground engaging surface (e.g., side walls 132d) with at least one of the ground engaging surfaces being configured as a sensing surface (e.g., sensing surface 133) with the electrode assembly 208 being arranged thereon (FIG. 1B). Although in embodiments depicted herein, ground engaging structure 140 will be shown as comprising a generally wedge-shaped configuration, it should be noted that, in other embodiments, the configuration of ground engaging structure 140 may be adapted specific to various soil preparation and/or planting applications. For example, in applications such as tillage, the ground engaging structure 140 may comprise a generally circular or polygonal configuration or other suitable configurations with FIGS. 1A and 1B being but one exemplary embodiment.

As illustrated in FIG. 1A, in the wedge-shaped configuration, the ground engaging structure 140 can comprise a plurality of walls 132 each being formed of an electrically insulating material. The plurality of walls 132 may include a rear wall 132a, a lower wall 132b, an upper wall 132c, and side walls 132d (i.e., first and second ground engaging surfaces), which are interconnected and collectively arranged to define a generally tapered ground engaging structure structure. For example, as depicted in FIG. 1A, side walls 132d may converge and taper inwardly from the rear wall 132a to form a soil penetrating edge 138 that is configured to penetrate the soil. The upper wall 132c can be adapted for coupling to a support structure or frame (refer, e.g., to FIG. 5B), which allows for a large down force to be applied to the sensor 106 to firmly secure placement of the sensor in the soil and to ensure that sufficient soil contact is maintained. The upper wall 132c may also comprise at least one aperture 120 arranged thereon that is sized to receive a plurality of electrode wires 122 associated with each electrode sensing unit 128.

The lower wall 132b, which is arranged at an opposing end of sensor 106, may comprise a generally planar outer surface to help facilitate leveling of the soil as the sensor 106 is moved across the soil. Additionally, it should be noted that the generally tapered configuration of sensor 106 is particularly advantageous in that it not only increases measurement accuracy, but it also allows for the sensor to be operated as an implement or tool. For example, the sensor 106 may be configured to measure soil properties at various penetration depths while being simultaneously adapted to condition the soil.

To enable sensing, the electrode assembly having a plurality of electrode sensing units 228 may be disposed on the sensing surface 133 as discussed with reference to FIG. 1A. In embodiments, each of the plurality of electrode sensing units 228 can comprise at least three electrodes 224a-c spaced apart from one another by a dielectric 225, with each electrode being sized substantially similar and formed of a conductive material. In some embodiments, electrodes 224a-c may be arranged horizontally such that an x-y planar surface of each electrode is arranged generally perpendicular to an x-y planar surface of the ground engaging structure 140 (refer, e.g., to FIG. 1A). In other embodiments, electrodes 224a-c may be arranged vertically or in other suitable configurations specific to application and/or design requirements. Electrodes 224a-c may include a ground electrode (e.g., electrode 224b) disposed between an upper sensor electrode (e.g., electrode 224a) and a lower sensor electrode (e.g., electrode 224c), such that a first and a second electrode pair 227, 229 is formed. In some embodiments, the first electrode pair 227 may include the upper sensor electrode and the ground electrode, and the second electrode pair 229 may include the lower sensor electrode and the ground electrode. Since a common element, i.e., the ground electrode, is shared between each of the first and second electrode pairs 227, 229, two respective electrical circuits may be formed, which will be discussed in further detail with reference to FIG. 4.

In such a configuration, sensor 106 may be configured to detect changes in an electric field indicative of changing soil properties (e.g., varying moisture or temperature conditions) while the sensor 106 is immersed in the soil. For example, as the sensor 106 moves across a field, there will be a measurable change in an output signal based on the frequency response of the measured soil sample. As one example, the determined soil property may include soil moisture with the dielectric material including a mixture of both soil and water. In such a composition, because the dielectric of water (approximately 80) is much greater than that of other soil constituents (e.g., dry soil (~4) or air (~1)), the complex permittivity of the soil will be heavily influenced by its water content. As such, because the water content of the soil will alter the response of the applied field in a complex manner, the complex permittivity over various frequencies may be determined.

As will be appreciated by those skilled in the art, FIGS. 1A-1B are provided merely for illustrative and exemplary purposes and are in no way are intended to limit the present disclosure or its applications. In other embodiments, the arrangement and/or structural configuration of sensor 106 may vary. For example, although a single sensor 106 is shown in FIG. 1, in other embodiments, sensor 106 may comprise two or more sensors coupled together to form a dual sensor arrangement. In still other embodiments, ground engaging structure 140 may further comprise a generally slanted configuration, which may extend in an upward or downward direction with respect to the soil to facilitate increased soil preparation.

Figure 2:
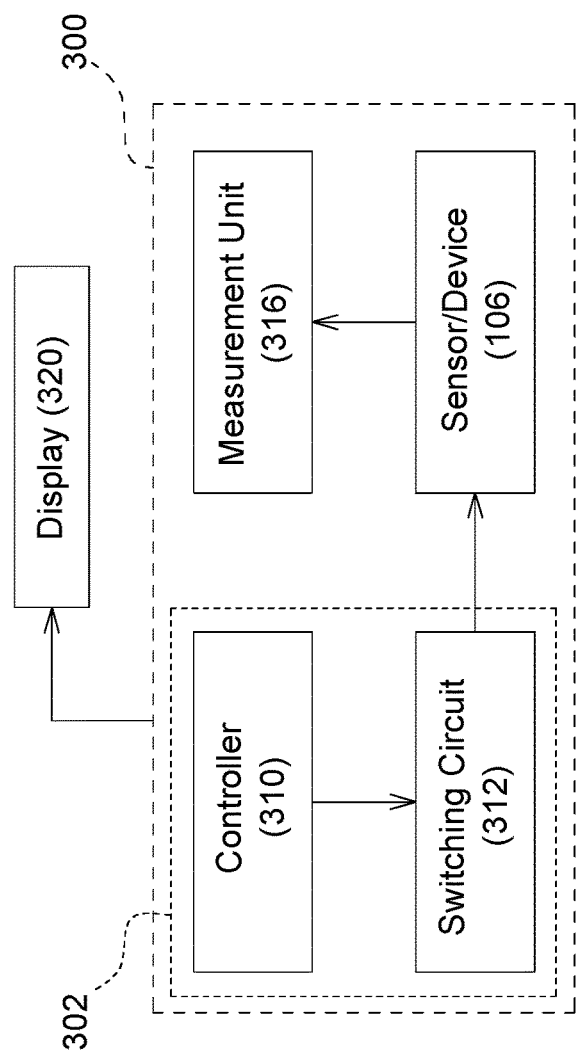
FIG. 2 is a block diagram of a sensor system according to an embodiment.
Figure 3A:
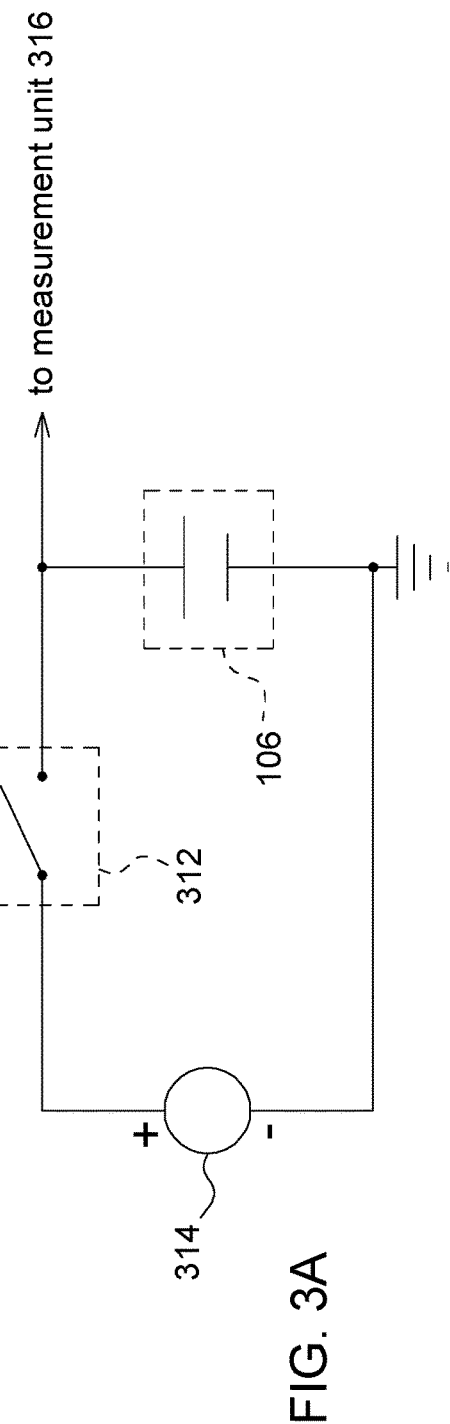
FIG. 3A is a schematic view of the electrical coupling of a sensor and a switching circuit of the sensor system of FIG. 2 according to an embodiment.

Referring to FIGS. 2 and 3A, a sensor system 300 is shown according to an embodiment. In embodiments, the sensor system 300 can comprise a control unit 302 and a measuring unit 316 operatively coupled to the sensor 106. The control unit 302 can comprise a controller 310 and a switching circuit 312 for controlling the operations of sensor 106. The controller 310 may include a microprocessor, microcontroller or other suitable programmable circuitry that is adapted to perform data processing and/or system control operations. For example, the controller 310 may be configured to generate a control signal that controls the switching operations of the switching circuit 312 in response to an operator's input.

Figure 3B:
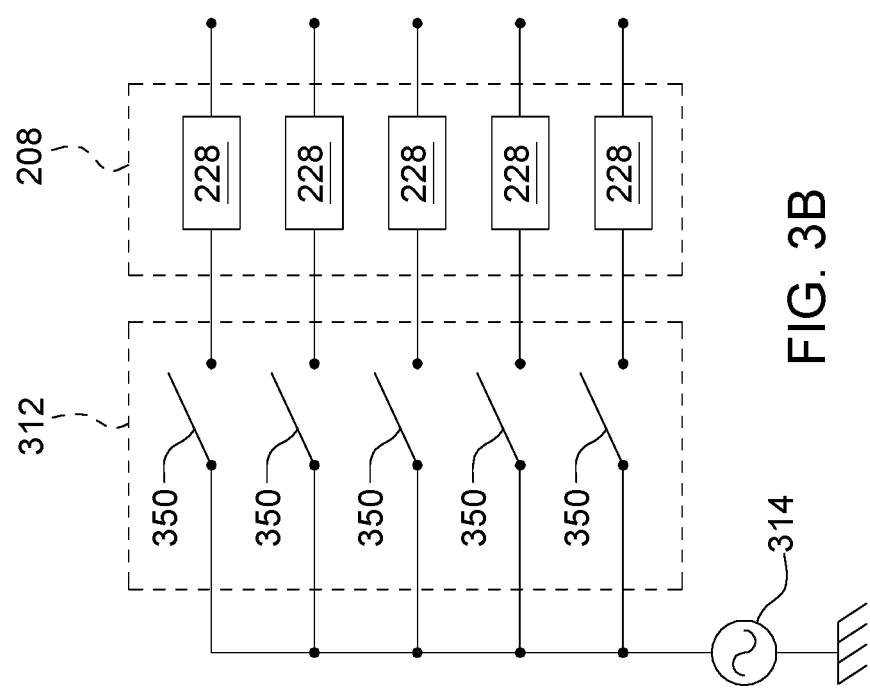
FIG. 3B is a schematic view of a switching circuit and electrode assembly according to an embodiment.

Upon receipt of the control signal generated by controller 310, the switching circuit 312, which is electrically coupled to an excitation source 314, operates to switch power from the excitation source 314 to the sensor 106 (e.g., by applying a sine wave of varying frequency). As depicted in FIG. 3B, in embodiments, switching circuit 312 can comprise a plurality of switching elements 350 coupled to an excitation bus 315 powered by excitation source 314. Each of the plurality of switching elements 350 can be individually coupled to each of the electrode sensing units 228 arranged within sensor 106, such that upon actuation, the switching elements 350 operate to selectively couple each electrode sensing unit 128 to the excitation bus 315, thereby enabling sensing by one or more electrode sensing units 128.

The plurality of switching elements 350 may include, for example, metal-oxide-semiconductor field effect transistors (MOSFET), diodes, bipolar junction transistors (BJT), PN transistors, NP transistors, NPN transistors, PNP transistors, combinations thereof, or other suitable switching devices. In some embodiments, each of the plurality of switching elements 350 may comprise a single switch, such as that shown in FIG. 3B, that is configured as a normally open switch that operates to close upon receipt of the control signal, thereby activating electrode sensing units 228 of sensor device 106. In other embodiments, switching elements 350 may respectively comprise two or more switches coupled in series such that in the event of an operational failure or for troubleshooting purposes one of the switches may operate as the controlling switching element. Additionally, although switching circuit 312 is shown as being located remotely from the sensor 106, in other embodiments, the location and layout of switching circuit 312 may vary. For example, in some embodiments, switching circuit 312 may be integrally arranged within the ground engaging structure 140 of sensor 106.

In embodiments, the measurement unit 316 can comprise a capacitance meter, an impedance meter or other measuring device for detecting changes in an electrical output signal (i.e., $S_0$ or $S_1$) generated by sensor 106. The electrical output signal can comprise a complex signal (e.g., the complex impedance) having both real and imaginary components which are used to determine soil moisture and/or other related soil properties (e.g. soil fertility). For example, the measurement unit 316 may measure a change in the electrical output signal with respect to a first observed reference measurement at a rest state when the sensor is not in the ground and a second observed reference measurement during a testing state when the sensor 106 is inserted into the ground. In one embodiment, the measurement unit may be coupled to the controller 310 for processing to determine the difference or change in the electrical output signal, where a display 320 is coupled to the controller 310 for displaying the difference or change in the electrical output signal. In other embodiments, the measurement unit 316 may be configured as a separate stand-alone unit.

Figure 4:
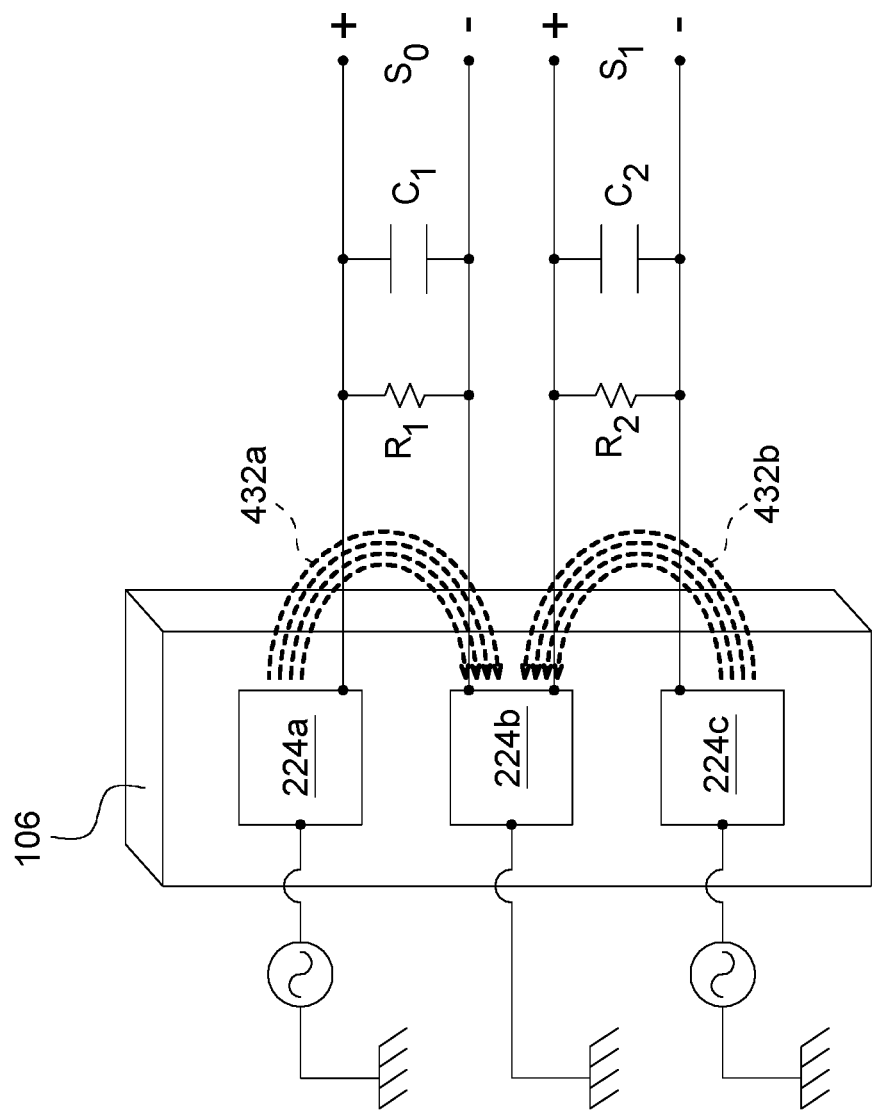
FIG. 4 is a schematic view of a sensor according to an embodiment.

Referring to FIG. 4, a schematic view of an electrode sensing unit arranged within sensor 106 and a corresponding fringing electric field distribution is shown. As previously discussed, each electrode sensing unit 228 may comprise two respective electrical circuits each including an ideal capacitor (e.g., C1, C2) coupled in parallel with an ideal resistor (e.g., R1, R2). A first circuit 428 having a first output signal $S_0$ is formed by the first electrode pair 227, and a second circuit 430 having a second output signal $S_1$ is formed by the second electrode pair 229. Upon switching of switching elements 350, an electrical potential is applied to the electrode sensing units 228 via excitation source 314 and at least two fringing electric fields each having a plurality of field lines 432a, 432b are induced between the first and second electrode pairs 227, 229. The plurality of field lines 432a, 432b extend from the outer edges of each of the electrodes 224a-c in a direction generally perpendicular to an outer planar surface of ground engaging structure 140. As depicted, the first set of field lines 432a extend between the outer edges of the first electrode pair 227 in a first direction, and the second set of field lines 432b extend between the outer edges of the second electrode pair 229 in a second direction, with the first and second directions being determined based on a direction of current flow.

The electrodes 224a-c are arranged such that when the fringing electric field is projected into the soil, a fringe effect (i.e., distortion of the electric field along the outer edge of the electrodes) is produced in response to changing soil conditions (e.g., increased temperature or moisture). Notably, the sensor 106 is highly responsive to changes in the dielectric properties of the soil sensed between each of the electrodes 224a-c. For example, when the dielectric of the sensed medium (i.e., soil) is greater than the dielectric disposed between each electrode pair (i.e., air), the output signal detected by measurement unit 316 will increase.

Figure 5A:
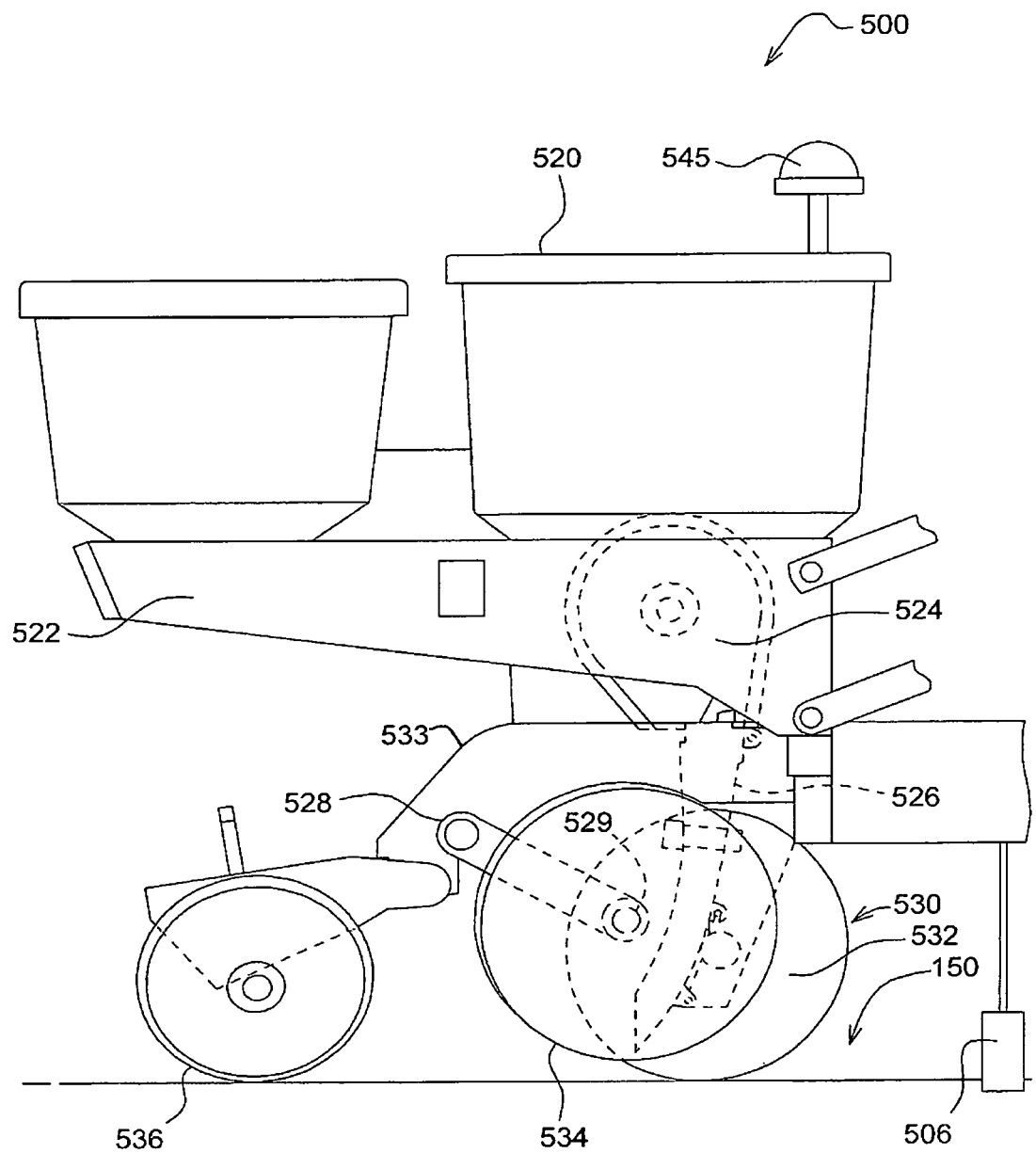
FIG. 5A is a side view of the sensor of FIG. 1A incorporated into an agricultural implement according to an embodiment.
Figure 5B:
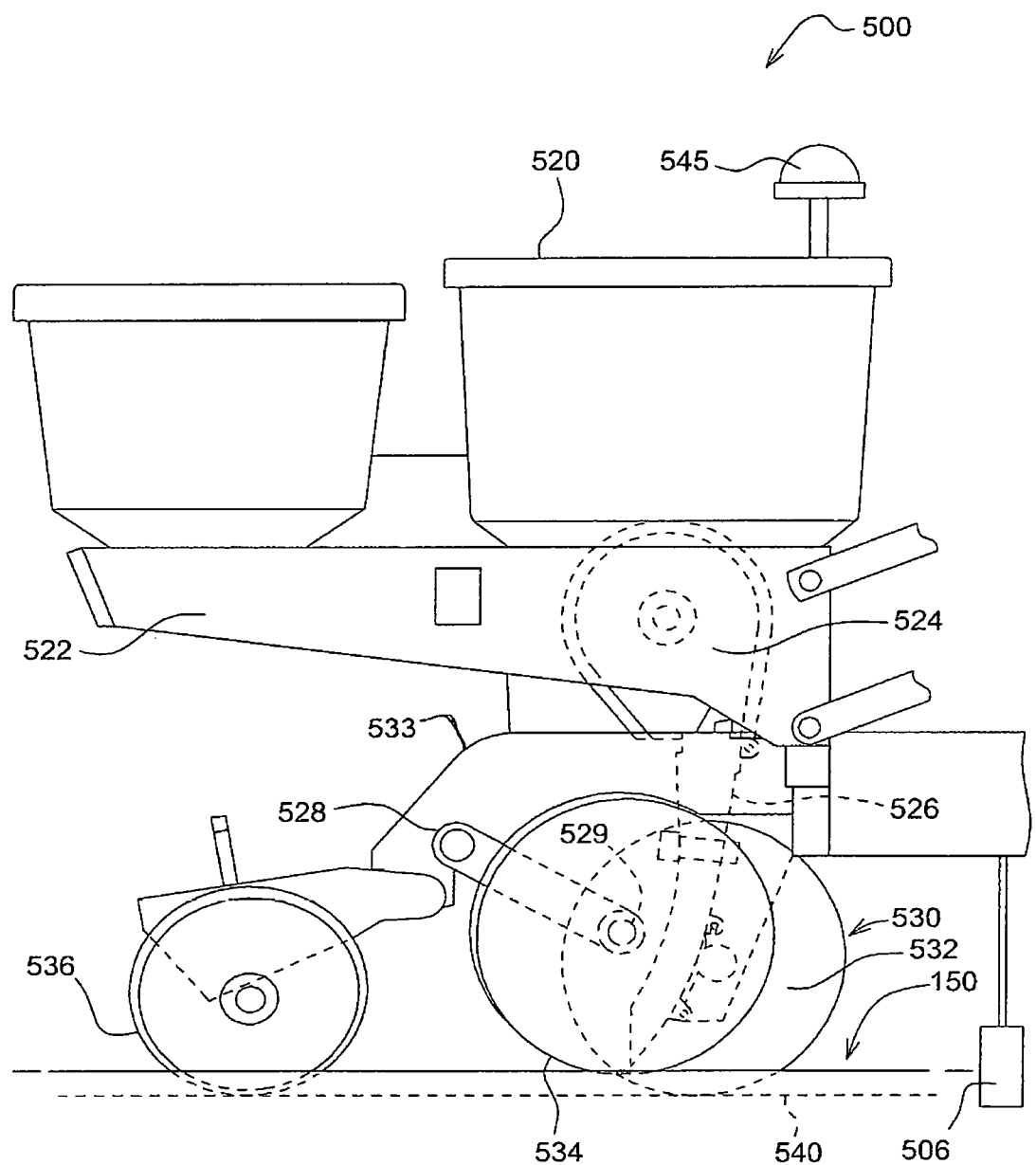
FIG. 5B is a side view of the sensor of FIG. 1A incorporated into an agricultural implement according to an embodiment.

In FIGS. 5A and 5B, an illustration of a planter unit 500 including a sensor 506 of a sensor system 300, which is substantially similar to sensor 106 discussed with reference to FIG. 1A, is incorporated is shown according to an embodiment. It should be noted, however, that although sensor system 300 is depicted as being incorporated into planter unit 500, in other embodiments, sensor system 300 may be incorporated into other agricultural applications, such as, e.g., tillage, air seeding, grain drilling, or others. In embodiments, the planter unit 500 can comprise a hopper 520 arranged in a generally upright position and mounted to a frame 522. A metering unit 524 having a generally circular configuration can be arranged beneath hopper 520 and can be configured to distribute seeds received from hopper 520 into a seed tube 526. The seed tube 526 directs the seeds received from the metering unit 524 to a soil opening 540 formed in the soil 550 by a ground engaging device 530. In some embodiments, ground engaging device 530 can comprise at least one opener disc 532 that is rotatable about a center axle and arranged to form the soil opening 540, whereas, in other embodiments, two or more opener discs 532 may be utilized according to design and/or specification requirements.

As depicted, in some embodiments, the sensor 506 of sensor system 300 may be arranged forward of the ground engaging device 530 and may be operably coupled to a support structure such as extension bar (not shown). In other embodiments, however, the location and arrangement of sensor 506 may vary, e.g., according to the type of agricultural implement employed. The extension bar (not shown) may be configured to operate (i.e., lower and raise) collectively with a height adjusting arm 528, the operation of which is controlled by a user such as a vehicle operator. The height adjusting arm 528 can be operably coupled to at least one gauge wheel 534 mounted proximate the ground engaging device 530 and may be configured to regulate the penetration depth of ground engaging device 530 via the height adjusting arm 528. For example, the height adjusting arm 528 enables the vertical position of the gauge wheels 534 to be adjusted relative to the ground engaging device 530, which establishes the depth at which the ground engaging device 530 is inserted into the soil (i.e., the depth of the soil opening 540). To vertically adjust the gauge wheels 534, the height adjusting arm 528 having a lower bearing surface 529 engages against at least one of gauge wheels 534 and is secured to the frame 522 by a lower bracket 533. A closing wheel assembly 536 can be arranged following of gauge wheels 534 and sensor 506 and is operable to close the soil opening 540 formed by ground engaging device 530. In other embodiments, planter unit 500 may further comprise a location-determining receiver 545, such as a satellite navigation receiver, that is mounted to the planter unit 500 and configured to provide field location data. For example, the location-determining receiver 545 can be used to determine the field location where each soil measurement is taken such that a 2-dimensional or 3-dimensional plot of the field location and corresponding capacitance measurement may be generated.

In operation, a vehicle operator will first adjust the height of gauge wheels 534 by applying a suitable down force, which, in turn, will lower each of the ground opening device 530 and sensor 506 into the soil. The vehicle operator will then activate each of the electrode sensing units 228 by inputting a control command via display 320 that is received by controller 310. In response, controller 310 generates the control signal that selectively activates each of the electrode sensing units 228 via switching circuit 312. In some embodiments, the controller 310 may be configured to generate a control signal that sequentially activates each electrode sensing unit 228 via switching elements 350. In other embodiments, each of the electrode sensing units 228 may be activated independently or activated in combination with other selected electrode sensing units based, e.g., upon a desired operational outcome or according to an operator's preference.

As discuss with reference to FIG. 4, upon activation, a plurality of electric fields (e.g., fringing electric fields) are generated by the various electrode sensing units 128, thereby enabling sensing by sensor 106. Each of the plurality of fringing electric fields will project outwardly in a direction generally perpendicular to the sensing surface 133 of sensor 106 as illustrated in FIG. 4. At a rest state (i.e., when the sensor 106 is located above the soil), a first observed reference measurement may be taken by measurement unit 316, and a second observed reference measurement may be taken in a testing state once the sensor 506 is inserted into the ground as shown in FIG. 5B. Each of the first and second observed reference measurements may be used to provide calibration information for the sensor 506 during operational use. For example, during operation, various sensor measurements will be taken and compared against each of the first and second observed reference measurements to determine an overall measurement value.

Once the planter unit 500 is in operation, the fringing electric fields generated by the electrode sensing units 228 distort in response to the changing dielectric properties of the soil, which results in a change in the complex electrical signals measured by measurement unit 316. For example, the increasing or decreasing moisture content or nutrient levels of the soil and their related properties influence the fringing electric field. As such, each of the plurality of electrode sensing units 228 of sensor 506 are configured to output an electrical signal $S_0$ or $S_1$ varying frequencies, which corresponds to an electrical parameter (e.g., resistance, capacitance, conductivity, dielectric constant) that may be used to determine the distinguishing soil properties and conditions at various penetration depths. In other words, the complex impedance (real and imaginary components) at several drive frequencies and voltages between the each of the selected electrode pairs is measured and used to determine soil moisture and other related soil properties (e.g., soil fertility, soil temperature, soil strength) in real time or based on a stored value. It should also be noted that the spacing and positioning of each electrode sensing unit 128 determines the depth and soil penetration distance. For example, the soil properties measured by electrode sensing units 228 arranged in an upper half of sensor 506 may exhibit different properties (e.g., varying moisture contents or temperatures) than those measured by electrode sensing units 228 arranged in a lower half of sensor 506.

Without in any way limiting the scope, interpretation, or application of the claims appearing below, a technical effect of one or more of the example embodiments disclosed herein is a sensor system and method for determining properties of soil at various penetration depths. While the present disclosure has been illustrated and described in detail in the drawings and foregoing description, such illustration and description is not restrictive in character, it being understood that illustrative embodiment(s) have been shown and described and that all changes and modifications that come within the spirit of the present disclosure are desired to be protected. Alternative embodiments of the present disclosure may not include all of the features described yet still benefit from at least some of the advantages of such features. Those of ordinary skill in the art may devise their own implementations that incorporate one or more of the features of the present disclosure and fall within the spirit and scope of the appended claims.

What is claimed is:

1. A sensor for determining soil properties, the sensor comprising:
    a wedge-shaped ground engaging structure adapted for coupling to an agricultural implement and to penetrate soil at a predetermined depth, the wedge-shaped ground engaging structure comprising a soil penetrating pointed edge, and at least one tapered planar sensing surface that is a side wall of the wedge-shaped ground engaging structure and that is arranged to extend from the soil penetrating pointed edge for engagement with the soil; and
    an electrode assembly disposed on the tapered planar sensing surface or within the wedge-shaped ground engaging structure, the electrode assembly comprising a plurality of electrode sensing units extending from the soil penetrating pointed edge and arranged in conductive strips of electrodes that are spaced apart with respect to one another, wherein each of the electrode sensing units are activated sequentially or activated in combination with a selected one of the electrode sensing units to selectively generate an electric field or electric fields that project outwardly into the surrounding soil in response to receipt of an excitation signal, wherein each of the electrode sensing units comprises at least three of the electrodes horizontally spaced apart from one another by a predetermined distance to form a first electrode pair and a second electrode pair with the electric field or the electric fields extending between the first electrode pair, or between the second electrode pair, or between the first electrode pair and the second electrode pair, and wherein the of electrode sensing units are configured to sense changes in the electric field or the electric fields corresponding to a change in a measured electrical output signal that is used to determine one or more soil properties and obtain a depth profile of soil conditions during movement of the agricultural implement in a field.

2. The sensor of claim 1, wherein the measured electrical output signal comprises a complex signal having both a real and an imaginary component.

3. The sensor of claim 2, wherein the real component corresponds to a measured resistance that is used to determine a first electrical parameter of the soil indicative of a first soil property, and wherein the imaginary component corresponds to a measured capacitance that is used to determine a second electrical parameter of the soil indicative of a second soil property.

4. The sensor of claim 3, wherein the first electrical parameter comprises an electrical conductivity and the second electrical parameter comprises a dielectric constant.

5. The sensor of claim 3, wherein the first or second soil property includes at least one of soil moisture content, soil fertility, soil temperature, soil strength, or combinations thereof.

6. The sensor of claim 1, wherein the first and second electrode pair of each of the plurality of electrode sensing units are sequentially activated via a control unit to induce generation of the electric field.

7. The sensor of claim 1, wherein the electric field extends in a direction generally perpendicular to the sensing surface.

8. The sensor of claim 1 further comprising a switching circuit electrically coupled to the electrode assembly.

9. The sensor of claim 1, wherein the ground engaging structure comprises a wedge-shaped configuration having at least two side walls that are arranged to converge at one end to define the soil penetrating edge that extends in a direction of travel of the agricultural implement.

10. The sensor of claim 1, wherein the ground engaging structure comprises a disc or polygonal structure.

11. A sensor system for determining soil properties, the sensor system comprising:
    a sensor comprising a wedge-shaped ground engaging structure having a soil penetrating pointed edge, a tapered planar sensing surface that is a side wall of the wedge-shaped ground engaging structure and that is arranged to extend from the soil penetrating pointed edge, and a plurality of electrode sensing units arranged in conductive strips of electrodes that are spaced apart with respect to one another on the tapered planar sensing surface or within the wedge-shaped ground engaging structure, each of the electrode sensing units extending continuously from the soil penetrating pointed edge, wherein the sensor is adapted for coupling to an agricultural implement and to penetrate soil in the direction of travel of the agricultural implement;
    a control unit coupled to the sensor, the control unit comprising a controller and a switching circuit, wherein the controller is configured to generate a control signal to control operations of the switching circuit to enable selective activation of each of the electrode sensing units, each of the electrode sensing units comprising at least three of the electrodes that are horizontally spaced apart from each other form a first electrode pair and a second electrode pair, such that an electric field extends between at least two of the electrodes, and wherein the control unit is configured to sequentially activate the electrode sensing units to generate the electric field or to activate in combination selected ones of the electrode sensing units; and a measurement unit communicatively coupled to the control unit, wherein the measurement unit is configured to detect changes in the electric field corresponding to a change in a measured electrical output signal as the sensor is moved throughout the soil, and wherein the measurement unit is configured to correlate the change in the measured electrical output signal to a change in a dielectric of the soil with respect to a reference measurement to determine soil properties and obtain a depth profile of soil conditions during movement of the agricultural implement in a field.

12. The sensor system of claim 11 further comprising a display unit configured to display a profile of a measured soil property as a function of depth.

13. The sensor system of claim 11 further comprising a location-determining receiver configured to receive field location data, wherein the field location data is used to generate a plot of a measured capacitance versus a field location.

14. The sensor system of claim 11, wherein the measured electrical output signal comprises a complex signal having both a real and an imaginary component, wherein the real component corresponds to a measured resistance that is used to determine a first electrical parameter of the soil indicative of a first soil property, and wherein the imaginary component corresponds to a measured capacitance that is used to determine a second electrical parameter of the soil indicative of a second soil property.

15. The sensor system of claim 14, wherein the first or second soil property comprises one or more of the following: a soil moisture content, a soil temperature, soil fertility, and a soil strength.

16. A method for determining soil properties, the method comprising:
providing an electrode assembly comprising a plurality of electrode sensing units arranged in conductive strips of electrodes spaced apart from one another on or within a sensing surface that is a tapered planar side wall of a wedge-shaped ground engaging structure adapted for coupling to an agricultural implement and having a soil penetrating pointed edge, each electrode sensing unit extending from the soil penetrating pointed edge, and an electrically insulating material, wherein each of the plurality of electrode sensing units comprises at least three of the electrodes horizontally spaced apart from one another by a predetermined distance to form a first electrode pair and a second electrode pair;
inducing an electric field between at least two electrodes arranged within each of the electrode sensing units by sequentially activating or activating in combination each of the electrode sensing units via a switching circuit selectively coupled to each of the electrode sensing units;
detecting changes in the electric field in response to a changing soil property, wherein the changes in the electric field correspond to a change in a measured complex signal;
determining a soil property based on the measured complex signal; and
generating a soil property profile as a function of depth.

17. The method of claim 16, wherein inducing the electric field further comprises electrically coupling an excitation source to at least one of the at least two sensor electrodes by actuating the switching circuit via a controller.

18. The method of claim 16, wherein determining a soil property further comprises determining a dielectric constant and an electrical conductivity of a measured soil sample of the changing soil property based on the measured complex signal.

19. The method of claim 16, wherein generating a soil property profile further comprises displaying at least one of a soil moisture content, a soil temperature, a soil strength as a function of depth.

* * * * *